United States Patent [19]

Hublot et al.

[11] Patent Number: 4,595,590
[45] Date of Patent: Jun. 17, 1986

[54] METHOD FOR PREVENTING OR TREATING PSEUDO-MEMBRANOUS COLITIS

[75] Inventors: Bernard Hublot, Paris, France; René H. Levy, Seattle, Wash.

[73] Assignee: Laboratoires Biocodex, Montrouge, France

[21] Appl. No.: 571,523

[22] Filed: Jan. 17, 1984

[51] Int. Cl.<sup>4</sup> ............................................. A61K 35/72
[52] U.S. Cl. ...................................... 424/93; 424/88; 435/940
[58] Field of Search ..................... 424/93, 88; 435/940

[56] References Cited

U.S. PATENT DOCUMENTS 4,138,479  2/1979  Truscheit et al. ...................... 424/88
4,265,913  5/1981  Eichelburg ........................ 424/93 X

FOREIGN PATENT DOCUMENTS 987880   1/1967  France ................................. 424/93
2096887  3/1972  France ................................. 424/93

OTHER PUBLICATIONS

Med. Chir. Dig. 1976, 5, 401–406, Anonymous.
Rev. Franc. Gastro-Enterol. 1975, 114, 45–50, Ligny.
Gastrointestinal Disease, Pathophysiology, Diagnosis, Management, Sleisinger et al. Eds., Saunders, 1983, 1168–1184, Bartlett.
Rev. Prat. 1982, 32, 2807–2819, Bories et al.
New Eng. J. Med. 298, 531–534 (1978), Bartlett et al.
Lancet, 1, 1063–1066 (1978), Larson et al.
Br. Med. J. 1, 695 (1978), George et al.
J. Clin. Nut. 33, 2527–2532 (1980), Fekety et al.
Gastroenterology, 79, 948–951 (1980), Peikin et al.
Gastroenterology, 81, 5–9 (1981), Viscidi et al.
J. Clin. Microbiol. 14, 26–31 (1981), Gilligan et al.
Gut, 22, 34–37 (1981), Listtman et al.
J. Infect. Dis. 136, 701–705 (1977), Bartlett et al.
Goodman and Gilman's The Pharmacological Basis of Therapeutics, Sixth Ed., pp. 1181 and 1186, Macmillan Publishing Co., Inc., NY.
Terence W. O'Connor, "Pseudomembranous Enterocolitis: A Historial and Clinical Review". Dis Colon Rectum, 1981; 24, pp. 445–448.

Primary Examiner—Howard E. Schain
Attorney, Agent, or Firm—Young & Thompson

[57] ABSTRACT

The invention relates to a method for preventing or treating pseudo-membranous colitis in a patient submitted to antibiotic treatment by means of Saccharomyces yeasts.

9 Claims, No Drawings

METHOD FOR PREVENTING OR TREATING PSEUDO-MEMBRANOUS COLITIS

BACKGROUND OF THE INVENTION

This invention relates to a method for preventing or treating pseudo-membranous colitis which comprises administering yeasts of the genus Saccharomyces.

Pseudo-membranous colitis (PMC) is a rare but severe disease, often mortal, which is generally caused by a toxin-producing germ of the genus Clostridium, especially *Clostridium difficile*, and which occurs mainly in patients who have been submitted to longer or drastic treatment by antibiotics (about 1% of the cases). PMC is a life-threatening disease which consists in production of pseudomembranes on the colon due to clostridial toxins. PMC has recently been recognized as a specific disease entity:

PMC contrary to its name, is not included in colitis which usually designates less severe diseases of the colon such as stomach ache with diarrhea, constipation, abdominal distension and the like;

PMC is particularly distinguished from antibiotic-associated diarrhea and certain forms of antibiotic-associated colitis;

(M. A. SANDE and G. L. MANDELL in GOODMAN and GILMAN'S, 6th Edition, p. 1186, Macmillan Publishing Co. Inc.;

T. W. O'CONNOR, Pseudomembranous Enterocolitis, Dis. Col. & Rect., Sept. 1981, 24, No. 6, p. 445-8).

Antibiotics such as clindamycin, lincomycin, ampicillin and the like have often been reported causing PMC (J. G. Bartlett et al., Antibiotic-associated colitis, Clinics in Gastroenterology, September 1979, vol. 8, No. 3 p. 783-801; F. J. Tedesco et al., Clindamycin and colitis., Ann. Intern. Med., 1975, 82, 279). Germs of the species *Clostridium difficile* or *Clostridium sordellii* and their toxins are usually found in the stools of patients who develop PMC.

Prior attempts have been made to cure this disease and several therapeutic agents were proposed particularly vancomycine or metronidazole (see Bartlett above, and J. R. D. Brown; Brit. Med. J. 283, p. 1334, Nov. 14, 1981).

The results were interesting but not sufficient inasmuch as relapse was often observed.

It is also known that yeasts of the genus Saccharomyces such as *Saccharomyces boulardii* or *Saccharomyces cerevisiae* have been used for long in the prevention and treatment of minor G.I. tract disturbances (antibiotic-associated diarrhea or colitis). These yeasts are generally administered via oral route in the form of capsules containing from 0.050 to 0.200 g of substance, the daily doses being usually of about 0.100 to 0.400 g for an adult.

However, it has never been proposed up to now that any type of yeast could treat PMC.

SUMMARY OF THE INVENTION

It has now been found that Saccharomyces, especially *Saccharomyces boulardii* significantly decreases the mortality due to Clostridium in antibiotic-treated hamsters and consequently can be used for preventing and treating pseudo-membranous colitis in man.

DETAILED DESCRIPTION OF THE INVENTION

As stated above, antibiotics such as clindamycine induce a mortal colitis in the Hamster. This colitis is characterized by multiplication of Clostridium germs elaborating a cytopathogenic toxin at the colon level. This animal colitis is widely recognized in the scientific litterature as being quite similar to the PMC in the human (see Bartlett above and R. A. Browne et al., John Hopkins Med. J. 1977, 141, 183-192). The experiments related herein show that a method for curing this disease has now been found by means of Saccharomyces.

Consequently, the object of the invention is a method for preventing or treating pseudo-membranous colitis in a human patient which comprises administering to the patient a therapeutically effective amount of yeasts of the genus Saccharomyces. Preferably, the yeasts are administered at 0.5-10 g daily dose (based on freeze-dried weight). Most preferably, the yeasts used are those of the *Saccharomyces boulardii* species.

The yeasts may be administered through nasal catheter or preferably in the form of dosage units for oral administration containing e.g. from 0.250 to 2.5 g of yeasts per dosage unit, for example in the form of capsules containing about 0.250 g or sachets containing about 0.250 to 2.5 g of yeasts. But of course other forms such as suspensions could be used.

The preferred embodiments of the invention are to provide a method for preventing or treating PMC in a human patient submitted to antibiotic treatment, which comprises administering to said patient a daily oral dose of 0.5 to 5 g of *Saccharomyces boulardii*.

The following examples illustrate the present invention.

EXAMPLE 1

Influence of *Saccharomyces boulardii* on clindamycin-induced mortality.

A single lethal dose ($LD_{90}$) previously determined as 1 mg/kg of clindamycin (Dalacin ®) was administered per os to the male Syrian Hamster (of Charles River Breeding Laboratory) weighing 90 to 100 grams.

*Saccharomyces boulardii* in freeze-dried form (Biocodex Laboratories, France) was administered every day to batches of 10 hamsters in their drinking water 3 days before to 10 days after they received 1 mg/kg of clindamycin; the mortality was noted every day for 30 days.

The results were summarized in the following Table.

| Batch No. | S. boulardii | Survival/10 animals | P value (Fisher) |
|---|---|---|---|
| 1 | 0 | 0 | — |
| 2 | 0.6 g/kg/day | 4 | N.S. |
| 3 | 6 g/kg/day | 8 | P < 0.01 |
| 4 | 20 g/kg/day | 8 | P < 0.01 |

These results show that the mortality was decreased by 40 to 80% when the animals received *S. boulardii*.

EXAMPLE 2

Effect of *Saccharomyces boulardii* on numeration of *Clostridium difficile*.

Batches of 2 hamsters each received 20 g/kg/day of *Saccharomyces boulardii* from day −3 to day +2 and/or 1 mg/kg of clindamycin on day 0; another batch (control) received no product.

On day 2, i.e. before possible death due to clindamycin, the animals were submitted to euthanasia by chloroform and the organs (caecum and colon) were collected for examination and germ count. The tests were repeated three times.

The results show that:

In control batches which receive neither clindamycin nor *S. boulardii*, and in batches which only received *S. boulardii* the macroscopic aspect of the caecum and colon is normal. The count of *Clostridium difficile* showed about $10^1$ to a maximum of $10^2$ germs.

In the batch which only received clindamycin, the caecum and colon are congested, distended and certain parts are haemorrhagic; the count showed $10^9$ to $10^{11}$ germs of *Clostridium difficile* depending on the animals and the test (average $10^{10}$ germs).

In the batch which received clindamycin and *S. boulardii* the organs have about the same appearance as those of the control animals. The count of *Clostridium difficile* showed that the number of germs has been substantially lowered in comparison to the preceding batch: 5 counts out of 6 gave a number of $\leq 10^7$ germs.

We claim:

1. A method for treating pseudo-membranous colitis caused by germs of the genus Clostridium in a human patient suffering therefrom, which comprises administering to the patient a therapeutically effective amount of yeasts of the genus Saccharomyces.
2. The method of claim 1, wherein the yeasts are administered at 0.5–10 g daily dose.
3. The method of claim 1, wherein the yeasts are of the *Saccharomyces boulardii* species.
4. The method of claim 1, wherein the yeasts are administered in the form of dosage units for oral administration containing 0.250–2.5 g of yeasts.
5. The method of claim 4, wherein the dosage unit is in the form of capsules containing about 0.250 g of yeasts.
6. The method of claim 4, wherein the dosage unit is in the form of sachets containing about 0.250 to 2.5 g of yeasts.
7. A method for treating pseudo-membranous colitis caused by germs of the genus Clostridium in a human patient suffering from the same after having been subjected to antibiotic treatment, which comprises administering to said patient a daily oral dose of 0.5–5 g of *Saccharomyces boulardii*.
8. A method as claimed in claim 1, in which said germs are of the species *Clostridium difficile*.
9. A method as claimed in claim 7, in which said germs are of the species *Clostridium difficile*.

* * * * *